United States Patent [19]

Helmer

[11] Patent Number: 5,135,519
[45] Date of Patent: Aug. 4, 1992

[54] OSTOMY MAINTENANCE APPARATUS

[76] Inventor: Bradley G. Helmer, P.O. Box 966, Morton, Ill. 61550

[21] Appl. No.: 625,317

[22] Filed: Dec. 10, 1990

[51] Int. Cl.$^5$ ............................................. A61F 5/44
[52] U.S. Cl. .................................. 604/332; 604/345
[58] Field of Search ..................... 2/48, 49 A, 94; 604/332, 337, 333-336, 338-395

[56] References Cited

U.S. PATENT DOCUMENTS

| | | | |
|---|---|---|---|
| 1,486,676 | 3/1924 | Nilssen | ................................ 2/94 |
| 1,543,104 | 2/1925 | Hoag . | |
| 2,584,249 | 2/1952 | Belcher . | |
| 3,624,686 | 11/1971 | Beals . | |
| 4,387,713 | 6/1983 | Calanni . | |
| 4,495,662 | 1/1985 | Miller . | |
| 4,533,355 | 8/1985 | Fair . | |
| 4,592,750 | 6/1986 | Kay . | |
| 4,705,512 | 11/1987 | Faucher . | |

Primary Examiner—Randy C. Shay
Assistant Examiner—R. Clarke

[57] ABSTRACT

An ostomy maintenance apparatus comprising a shielding member made of a flexible lightweight material and fastened around ostomates waist using a releasable securing arrangement, a receptacle having an opening and being releasably attachable to the shielding member using an attaching arrangement. The receptacle includes reinforcement at the opening for support to keep the opening from collapsing while in use and for supporting a disposable waste receiver in an open and receivable manner into which refuse during and resulting from ostomy maintenance procedures is received and disposed of in, and a closure arrangement at the receptacle opening for temporary conversion of receptacle to a storage receptacle for the shielding member and some ostomy supplies.

9 Claims, 8 Drawing Sheets

OSTOMY MAINTENANCE APPARATUS

BACKGROUND

1. Field of the Invention

The present invention relates generally to an apparatus for use by individuals, known as ostomates, whom require the use of an ostomy appliance device for the collection of bodily waste materials. More specifically, the present invention relates to an apparatus to assist ostomates in the maintenance of their ostomy and ostomy appliances.

2. Description of Prior Art

Many individuals for various medical reasons, not relevant herein, require that their digestive or urinary tracts be surgically terminated or altered at some point and brought through and attached to their abdominal wall to provide a new opening to expel their bodily waste products. This new opening is referred to as a stoma and the individual is know referred to as an ostomate.

The basic types of ostomy surgeries the present invention deals with are the colostomy, ileostomy and urostomy. A colostomy, for example, is a surgical procedure re-routing the large intestine and bringing an end out a small opening and attaching to the abdominal wall. An ileostomy is a surgical procedure re-routing the small intestine or ileum to bring the end out a small opening and attaching to the abdominal wall. Urostomies are the surgical re-routing of the urinary tract to expel bodily waste products through a stoma.

These surgical procedures can be either temporary or permanent, depending upon reason(s) for surgery and amount of existing tract left after surgery.

The ostomate has no control over when the stoma will expel bodily waste materials. Thus, the ostomate must utilize an ostomy appliance device to collect and store their bodily waste products expelled by their stoma until such a time the ostomate can empty their ostomy appliance device.

Ostomy appliance devices can be either disposable or of the reusable type and usually consist of three (3) components. The first a faceplate or flange which is adhered to the abdominal wall surrounding the stoma. This faceplate or flange can be worn anywhere from one up to several days depending upon appliance type or model, condition of skin underneath, and the level of activity the ostomate is subject to. The second component is a receptacle or pouch which is fastened to the faceplate or flange to collect and retain the bodily waste products after they are expelled from the stoma. The bottom of most pouches are formed with an opening to permit drainage of the pouch once it has filled. The third component is a clip-type device to allow the opening and closing of the pouch opening for drainage purposes.

Heretofore, when an ostomate removes their ostomy appliance for replacement or other reasons, a number of significant problems arise. Most ostomates have no control over their stoma and when they remove their ostomy appliance, the stoma may expel bodily waste materials uncontrollably. This is referred to as stomal discharge. When the ostomy appliance is removed for replacement or other reasons there is nothing there to receive the stomal discharge resulting in unsanitary, sometimes odorous and unpleasant clean-up measures afterwards, if awkward steps are not followed.

One method of removal and replacement is for the ostomate to sit backwards on a toilet with the ostomy appliance over the bowl of the toilet. This method is very awkward and in most cases unsanitary and unpleasant as well as very time consuming.

Another method is to remove and replace their ostomy appliance after bathing while still in the bathtub or shower stall. Again a mess can be created by stomal discharge although clean-up measures may be a little easier. There are drawbacks when using this method also for an ostomate might slip and fall on the slick surfaces of a shower stall or bathtub causing a serious injury to the ostomate. Also the ostomate must make sure the skin surface surrounding the stoma is dry before installing a new appliance or it won't adhere correctly.

And still another method of ostomy appliance removal and replacement is to lean forward over a sink or bathroom basin with the appliance over the front edge of the sink or basin. The ostomy appliance may then be removed and the stoma must then be kept over the front edge of the sink or basin to catch any stomal discharge that occurs. This method is the best to my knowledge, but there are still unpleasant clean-up measures to be performed once finished with ostomy appliance removal and replacement.

Another problem arising when the ostomy appliance has been removed is the time spent on proper hygiene of the stoma region. Proper hygiene is crucial to the stoma and the surrounding skin. If not enough time is spent on hygiene an irritation or infection can cause medical problems that must be dealt with by a physician or qualified nurse. Age, health, handicap and skin condition of the stoma region all play a significant role in the length of time the ostomy appliance will be off. Thus, the longer the ostomy appliance is off the greater the chances are of stomal discharge to occur.

Furthermore, there is the psychological adjustment period after surgery the new ostomate must face up to. This period is crucial to the self-image of the new ostomate, having to face the fact that their body has been changed both physically and functionally and must now take care of something thing totally new to them. Books, support groups, and medical personnel have been the only means the new ostomate has of learning how to deal with their stoma. Until the new ostomate gets accustomed to removing and replacing their ostomy appliance with confidence of a good seal they need all the assurance they can get that their ostomy appliance is correctly in place and should not leak. This is usually accomplished by spending a lot of time on stomal maintenance and replacement of their ostomy appliance which results in stomal discharge occurring and creating messes to be cleaned up afterwards. The more messes a new ostomate makes while performing maintenance on their ostomy and ostomy appliance the harder it is and the longer it takes them to adjust to this new life style. It takes a long time to gain confidence and learn how to become efficient and avoid making a large mess while maintaining their ostomy and ostomy appliance correctly.

And still another problem facing the ostomate is the sanitary disposal of all refuse involved in the removal and replacement of their ostomy appliance and other maintenance procedures performed. Most of the refuse involved (used appliance, tape, wrappers, etc.) can not be flushed down the toilet, but must be discarded in the trash can. This is unsanitary and can become very odorous.

There is also the problem of keeping ostomy supplies from view of others. Ostomates are sensitive about having had their ostomy surgery and try to conceal all aspects of having had surgery from others not knowing of their ostomy, even their supplies are kept from view of others. Usually the ostomate keeps a drawer in the bathroom for their ostomy supplies, but their is always that nosy person that must look in everything.

The traveling ostomate also has that same problem of keeping ostomy supplies out of view of others while having those supplies close at hand in case of an emergency.

Yet still another problem the ostomate faces is while removing and replacing their ostomy appliance the need to move about the house may arise, for example answering the telephone or tending to a small child or infant. In this situation the ostomate would be unprotected from stomal discharge and the mess it may cause unless the stoma is covered with a towel or wash cloth and held there by hand.

Physicians also have a problem when seeing a patient who is an ostomate. If the physician needs the ostomate to remove their ostomy appliance for an examination, the physician must use towels or sheets to cover the ostomate to protect them from stomal discharge.

Most ostomates, therefore would find it desirable to have the present invention for use in the removal and replacing of their ostomy appliance and other maintenance procedures, involving their stoma and ostomy appliances, while having to deal with the for-mentioned problems.

OBJECTS AND ADVANTAGES

There is a lack of provisions available for ostomates to suitably deal with the significant problems they face when removing and replacing their ostomy appliance, as well as performing other maintenance procedures of the ostomy appliances and stoma of the ostomate.

Accordingly several objects and advantages of the present invention are:

(a) to provide an ostomy maintenance apparatus which is to be worn by an ostomate around their waist while removing and replacing their ostomy appliance as well as performing other maintenance procedures to their stoma;

(b) to provide an ostomy maintenance apparatus which when correctly installed around the ostomates waist, and before the start of removal and replacement of their ostomy appliance and other stoma maintenance procedures, will protectively shield the ostomate from becoming soiled by any refuse involved during the maintenance procedures;

(c) to provide an ostomy maintenance apparatus which when correctly installed around the ostomates waist, before the start of removal and replacement of their ostomy appliance, will collectively catch and store, inside a disposable waste receiver, any stomal discharge occurring during this maintenance procedure until a new ostomy appliance has been installed, at which time the disposable liner is sealed and discarded by the ostomate in the trash;

(d) to provide an ostomy maintenance apparatus which when correctly installed around the ostomates waist, before the start of removal and replacement of their ostomy appliance, will collectively hold for disposal, inside a disposable liner, any refuse (such as used ostomy appliance, tape, wrappers, tissues, etc.) involved during the removal and replacement of their ostomy appliance, until a new ostomy appliance has been installed;

(e) to provide an ostomy maintenance apparatus which when correctly installed around the ostomates waist, before the start of ostomy appliance removal and replacement or other maintenance procedures involving the stoma, will allow the ostomate as much time as needed to perform hygiene to the stoma and surrounding skin while being protected from any stomal discharge that may occur and consequently soil them or their clothing;

(f) to provide an ostomy maintenance apparatus which can be worn by an ostomate whether partially clothed or naked;

(g) to provide an ostomy maintenance apparatus which will help a new ostomate adjust psychologically to their new stoma and altered bodily functions by allowing the new ostomate to spend as much time as needed removing and replacing their ostomy appliance without creating a large mess resulting in unpleasant clean-up measures;

(h) to provide an ostomy maintenance apparatus that will assist a new ostomate in learning an efficient routine for maintenance procedures involving their ostomy, whereby the new ostomate builds up their confidence that the ostomy appliance has been installed correctly and should not worry about a leaking ostomy appliance;

(i) to provide an ostomy maintenance apparatus which will provide the ostomate a sanitary and efficient means for disposal of all waste material involved in removal and replacement of their ostomy appliance;

(j) to provide an ostomy maintenance apparatus which in part can be converted to a storage case for the remaining portion of the apparatus to be stored and concealed in a cosmetically attractive way;

(k) to provide an ostomy maintenance apparatus which in part can be converted to a storage case for the remaining portion of the apparatus and some ostomy appliance supplies to be stored and concealed in a cosmetically attractive way, whereby keeping ostomy appliance supplies from the view of others;

(l) to provide an ostomy maintenance apparatus which is compact enough for an ostomate to keep relatively close by for use at all times in case of an emergency involving the ostomates ostomy appliance;

(m) to provide an ostomy maintenance apparatus which is washable and re-useable;

(n) to provide an ostomy maintenance apparatus which is easily and economically manufactured;

(o) to provide an ostomy maintenance apparatus which may be used by ostomates without regards to the location of their stoma on their abdomen;

(p) to provide an ostomy maintenance apparatus which may be used by the ostomate as an ostomy maintenance kit for when traveling, stay overnight away from home, or as an emergency kit to keep at work, in their automobile or places the ostomate frequents on a regular basis; and (q) to provide an ostomy maintenance apparatus which can be used by physicians upon ostomate patients during stomal examinations or during other examinations requiring the removal of the ostomy appliance of the patient;

The present invention will be more fully understood, while further advantages will become apparent to someone skilled in the art of the present invention by reference to the following detailed description of one preferred embodiment thereof taken in conjunction with the accompanying drawings, in the several figures of which, like reference numerals identify like elements and closely related parts have the same reference numeral but different alphabetical suffixes.

BRIEF DESCRIPTION OF THE DRAWING FIGURES

FIG. 8 and FIG. 9 are plan views of the front and back panels of material the main body of convertible receptacle can be constructed from.

REFERENCE NUMERALS

Figure 1:
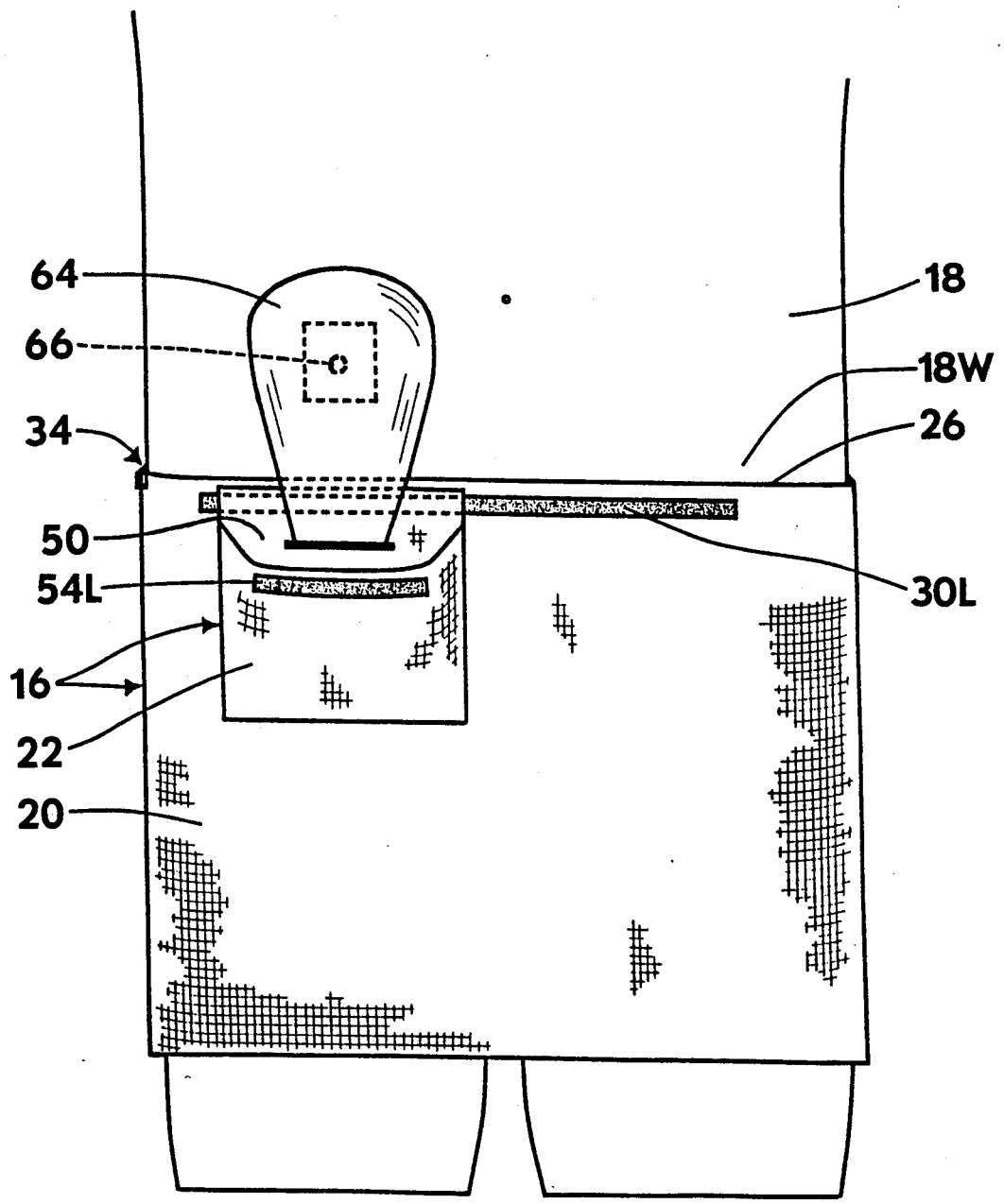
FIG. 1 is a pictorial view of an apparatus, constructed in accordance with the principles of the present invention, in place upon an ostomate, ostomy appliance fixed upon the ostomate.

16—apparatus
18—ostomate
18W—waist of ostomate 18
20—shielding member
20A—inner surface of 20
20B—outer surface of 20
22—convertible receptacle
24—panel of material
26—upper horizontal edge of 20
26A—lower horizontal edge of 20
28—vertical edge of 20
28A—vertical edge of 20
30L—loop segment of "Velcro" releasable adherence material in releasable attaching arrangement 56
32—strap
34—adjustable releasable securing arrangement
36H—hook segment of "Velcro" releasable adherence material used in adjustable releasable securing arrangement 34
36L—loop segment of "Velcro" releasable adherence material used in adjustable releasable securing arrangement 34
38—end of strap 32 permanently fixed to 20
38A—free end of strap 32
40—upper corner of 20
40A—upper corner of 20
42—inner surface of 32
44—back panel of material of 22
44A—side edge of 44
44B—lower edge of 44
44C—side edge of 44
44T—upper edge of panel 44
46—front panel of material of 22
46A—side edge of 46
46B—lower edge of 46
46C—side edge of 46
46T—upper edge of panel 46
48—over edge locked stitching
50—upward facing opening of 22
52H—hook segment of "Velcro" releasable adherence material used in both releasable attaching arrangement 56 and closure arrangement 58
54L—loop segment of "Velcro" releasable adherence material used in closure arrangement 58
56—releasable attaching arrangement
58—closure arrangement
60—wire
62—hem
64—ostomy appliance
66—stoma
68—disposable waste receiver
70—side seams of 68
71A—flap of 68
71B—flap of 68
72—extra space

DETAILED DESCRIPTION OF DRAWINGS

Now referring to the drawings, of a preferred embodiment of the present invention, and initially FIG. 1, there is depicted an apparatus constructed in accordance with the principles of the present invention, and generally designated by the numeral 16, shown here in place upon ostomate 18.

Apparatus 16 is a shielding member 20 with a convertible receptacle 22 as shown here, releasably attached to shielding member 20. Shielding member 20 is releasably secured around waist 18W of ostomate 18 and generally covering a portion of the front lower torso of ostomate 18. Shielding member 20 is made of a fabric characterizing terry-cloth or towel-like fabric but may also be made of suitable material that is flexible and comfortable to wear.

Figure 2:
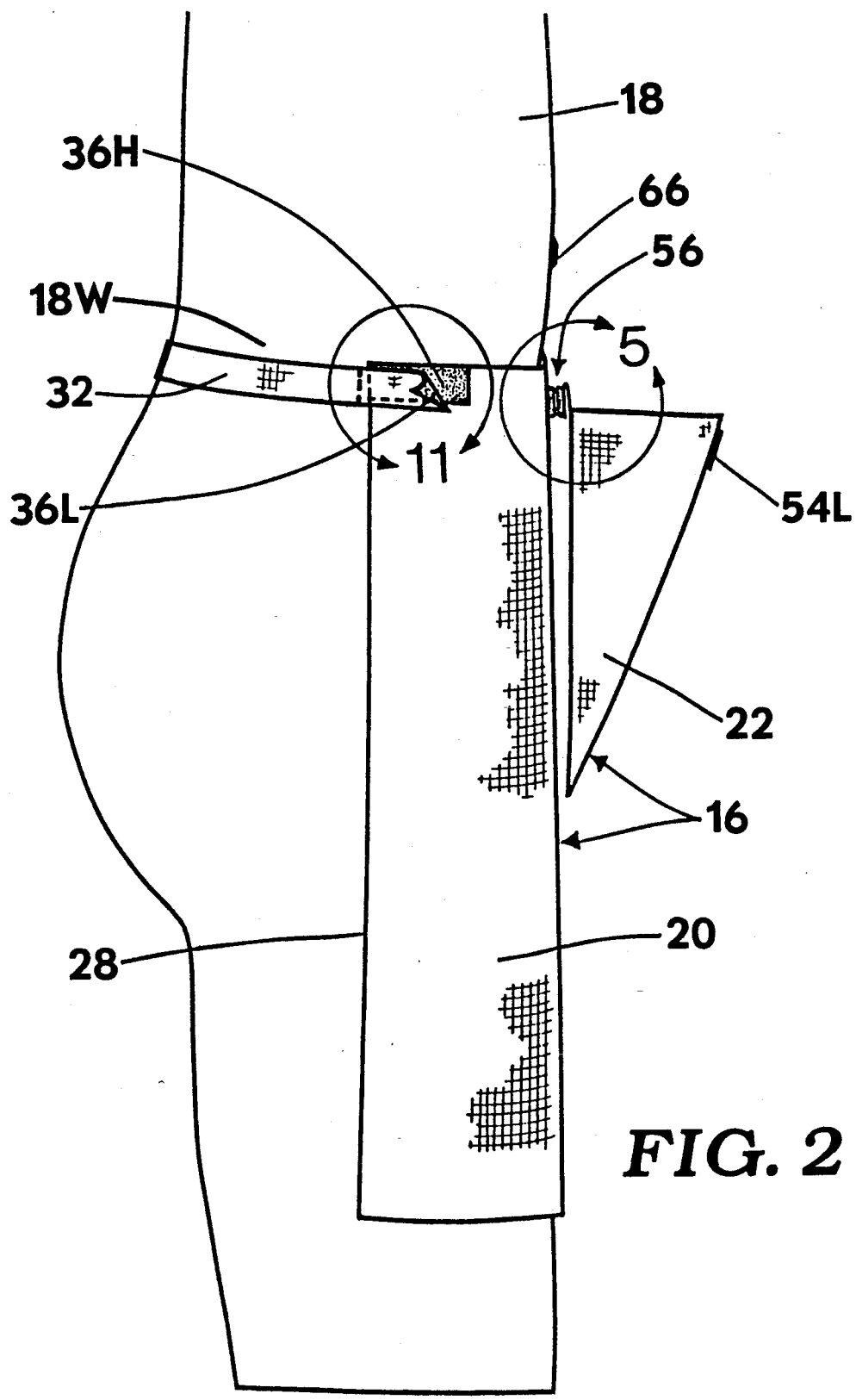
FIG. 2 is a side view of an apparatus, constructed in accordance with the principles of the present invention, in place upon an ostomate, ostomy appliance removed from ostomate.
Figure 3:
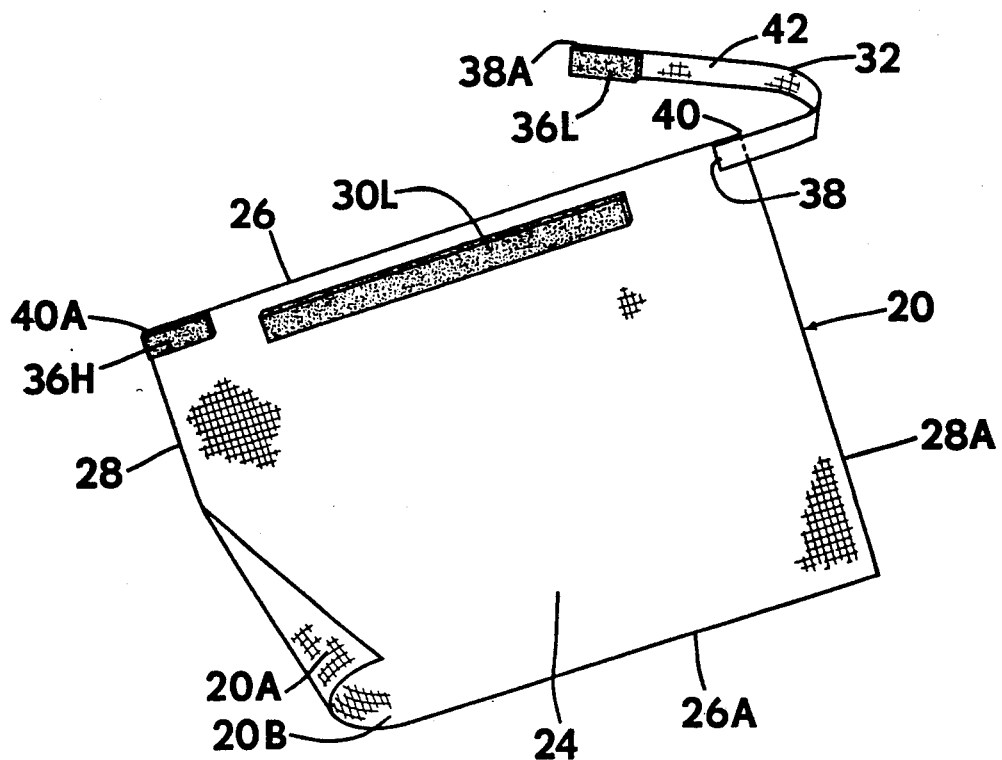
FIG. 3 is a plan view of the shielding member of the present invention.

As shown in FIG. 1, FIG. 2, and FIG. 3, shielding member 20 may be of generally rectangular shape and is of sufficient size to cover at least a portion of the front lower torso of ostomate 18.

Referring now to FIG. 3, shielding member 20 is a panel of material 24, shown here to be approximately 60 centimeters along horizontal edges 26 and 26A and approximately 45 centimeters along vertical edges 28 and 28A and having an inner side 20A and an opposite outer side 20B. Horizontal edges 26 and 26A along with vertical edges 28 and 28A form the perimeter of shielding member 20. Fixed upon shielding member 20, is a segment of releasable adherence material 30L bearing elements adherent to and releasable from a later described segment of releasable adherence material fixed upon convertible pocket 22.

The releasable adherence material used in the preferred embodiment of the present invention is of the type commercially available under the trademark "Velcro" and comprising of two differing segments of material adherent to and releasable from one another. These two segments differ from one another in that one segment is of a "fleecy" loop appearance and in this description of drawings, any numerical reference with a suffix "L" will be of the fleecy loop segment of this type of releasable adherence material. The second segment of this releasable adherence material is of a "burr-like" appearance having a multitude of tiny hook like projections and in this description of the drawings any numerical reference with a suffix of "H" will be of the burr-like segment of this type of releasable adherence material. By pressing these two differing segments together, loop surface facing hook surface, the segments adhere to one another. They may be released from one another by simply pulling the two segments apart. This type of releasable adherence material is quite durable and is capable of repeated adherences and releases from one another without adversely affecting its adherence capabilities, which is of importance in the preferred embodiment of the present invention, being used for releasably attaching convertible receptacle 22 to shielding member 20, and for releasably securing shielding member 20 around waist 18W of ostomate 18, and in the closure arrangement for temporary conversion of convertible receptacle 22 to a storage case as will be explained in following paragraphs.

There are other releasable fasteners that can be substituted as an alternative to the "Velcro" used in the preferred embodiment and a skilled artisan will be able to envision them.

Still referring to FIG. 3, segment 30L, of releasable adherence material is approximately 45 centimeters in length, 2 centimeters wide and fixed upon outer side 20B of shielding member 20, preferably stitched or sewn along its marginal edges, horizontally parallel and approximately 2 centimeters below upper edge 26 while being centered between vertical edges 28 and 28A.

Still referring to FIG. 3, and briefly FIG. 2, and FIG. 3 shielding member 20 is secured around waist 18W of ostomate 18 using adjustable releasable securing arrangement 34. Adjustable releasable securing arrangement 34 consists of strap 32, and releasable adherence material segments 36H and 36L. As depicted in FIG. 3, strap 32 is a length of stretchable elastic belt material approximately 25 centimeters long unstretched and 2 centimeters wide with end 38 permanently fixed upon either outer side 20B or inner side 20A, shown here fixed upon outer side 20B of shielding member 20 at upper corner 40. Included upon strap 32 is 36L, a 5 centimeter long by 2 centimeter wide segment of "Velcro" releasable adherence material, which is fixed, preferably stitched or sewn along its marginal edges, to inside surface 42 of strap 32 at end 38A. Segment 36H, which is the cooperating segment of "Velcro" releasable adherence material for 36L, is fixed, preferably stitched or sewn along its marginal edges, to upper corner 40A on outer side 20A of shielding member 20. Thus, segments of releasable adherence material 36H and 36L in combination with strap 32 are the preferred embodiment of the adjustable releasable securing arrangement 34 of the present invention, for releasably securing shielding member 20 around waist 18W of ostomate 18. The use of stretchable elastic material for strap 32 renders the securement of shielding member 20 to be adjustable to accommodate a variety of differing waist sizes of ostomates.

Figure 4:
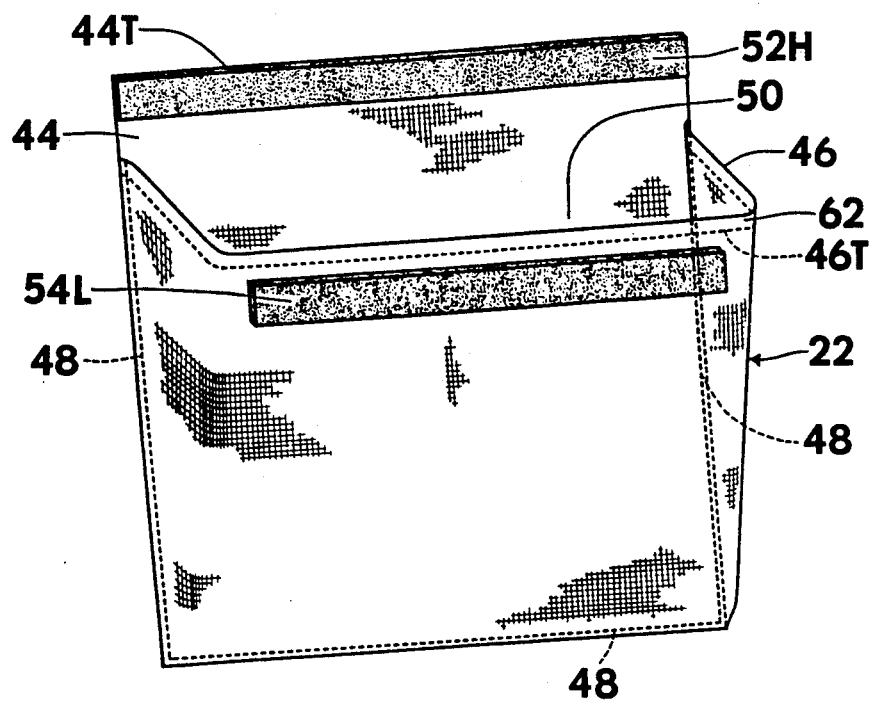
FIG. 4 is a plan view of the convertible receptacle of present invention.
Figure 8:
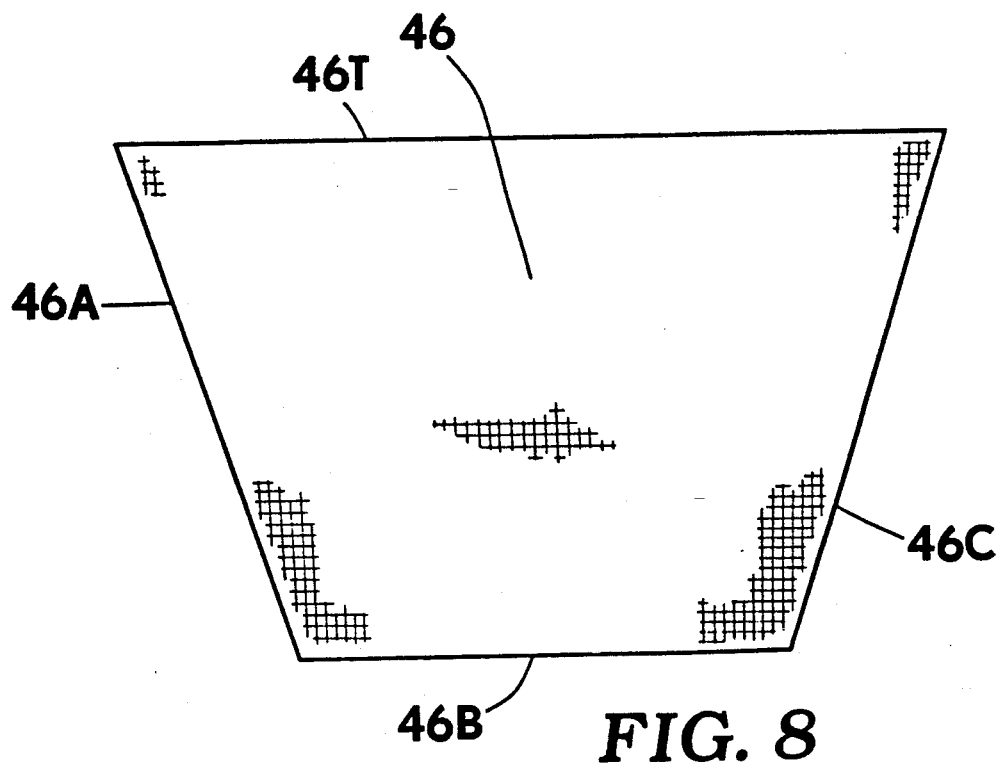
Figure 9:
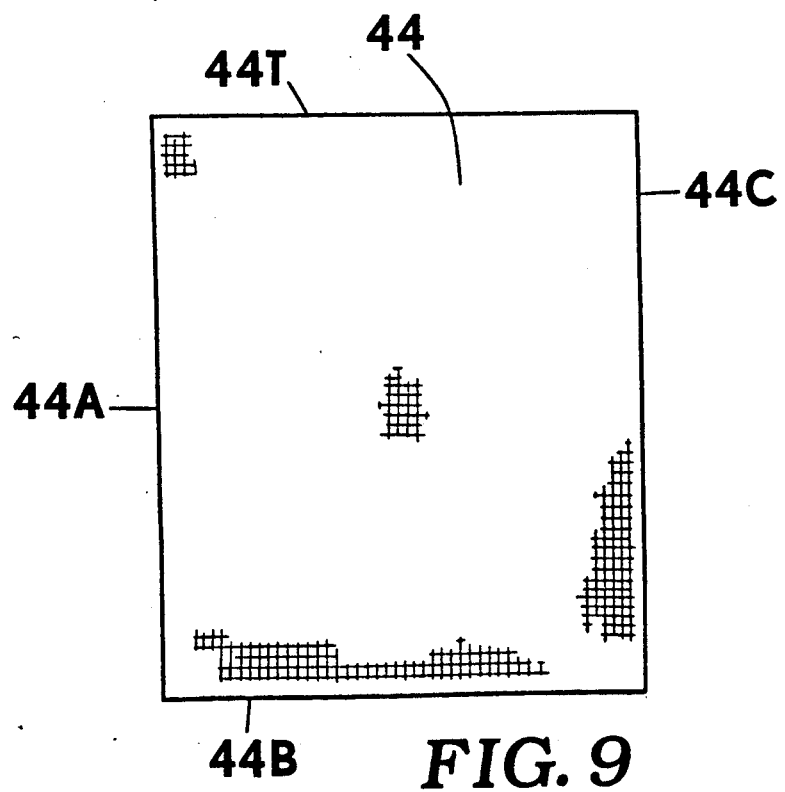

Now making reference to FIG. 4, FIG. 8, and FIG. 9, convertible receptacle 22 of the present invention, may be made of a flexible material resembling vinyl plastic tablecloth material. Convertible receptacle 22 is constructed of a back panel 44 of generally rectangular shape slightly longer vertically than a front panel 46. Front panel 46 is of generally isosceles trapezoidal shape having a slightly wider upper edge 46T than back panel 44 upper edge 44T and gradually narrows to become the same width at lower edge 46B as back panel 44 bottom edge 44B as shown in FIG. 8 and FIG. 9. Vertical edges and lower edges, of back and front panels 44 and 46, are connected or united together along their cooperating edges 44A to 46A, 44C to 46C, and 44B to 46B, preferably by sewn over-edge locked stitching 48, or other suitable stitching or bonding methods, to form main body of convertible receptacle 22 while leaving an upward facing opening 50 at the upper portion of the main body of convertible pocket 22. Upon convertible receptacle 22 will be 52H, a segment of "Velcro" releasable adherence material approximately 20 centimeters long and 2 centimeters wide, which is fixed preferably sewn or stitched, horizontally and adjacent to upper edge 44T of back panel 44 and on the front or side facing opening 50. Segment 52H extends the full length of upper edge 44T of back panel 44.

Also upon convertible receptacle 22 is 54L, which is another segment of "Velcro" releasable adherence material. Segment 54L is fixed, preferably sewn, horizontally and parallel to, and approximately 2 centimeters below, upper edge 46T of front panel 46, and on the front or side facing away from opening 50, of panel 46. Segment 54L is approximately 15 to 20 centimeters in length and 2 centimeters wide.

FIG. 2, FIG. 5, FIG. 10 and FIG. 12 illustrates that segment 52H is in part to both releasable attaching arrangement 56 and closure arrangement 58. Segment 52H, on convertible receptacle 22, in combination with segment 30L, on shielding member 20, form releasable attaching arrangement 56 used in releasably attaching convertible receptacle 22 to shielding member 20.

Figure 10:
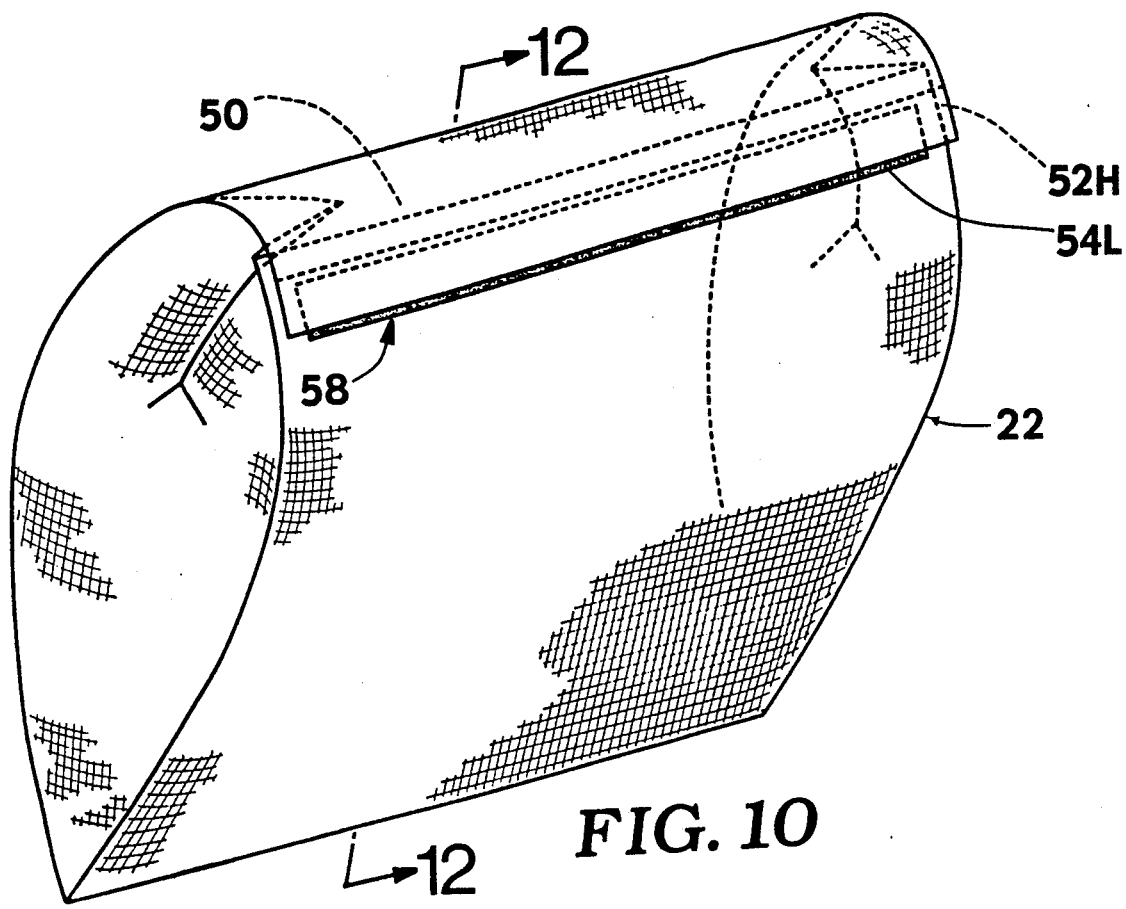
FIG. 10 is a view of convertible receptacle converted to and being used as storage receptacle for the shielding member of the present invention.
Figure 11:
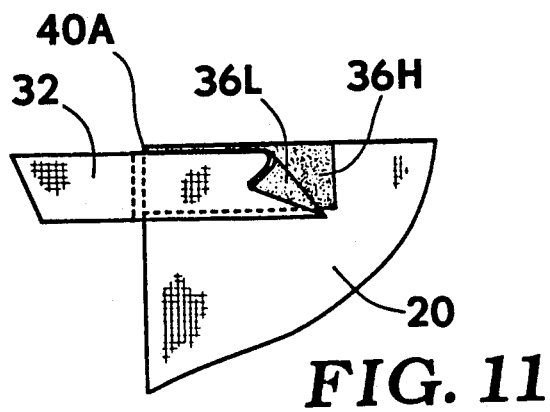
FIG. 11 is an enlarged sectional view of the releasable securing arrangement taken on line 11—11 of FIG. 2.
Figure 12:
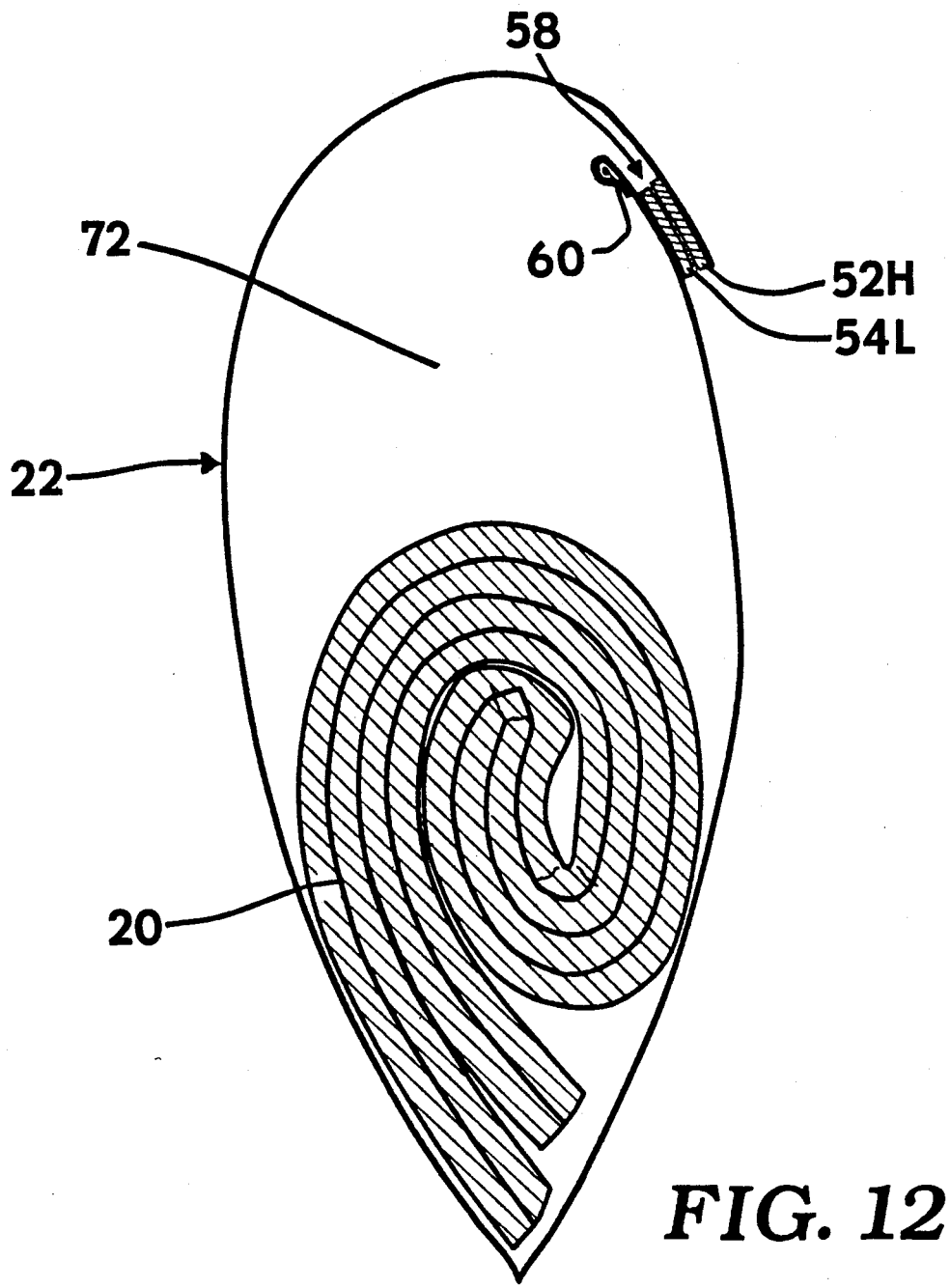
FIG. 12 is an enlarged sectional view of the releasable closure arrangement taken along lines 12—12 of FIG. 10, stored shielding member included inside convertible receptacle.

Segment 52H, on convertible receptacle 22, is also used in combination with segment 54L of convertible receptacle 22 in forming closure arrangement 58 used for temporary conversion of convertible receptacle 22 to a storage receptacle, as shown in FIG. 10 and FIG. 12. Releasable attaching arrangement 56 and closure arrangement 58 will be described in more detail in later paragraphs in the operation section.

Figure 5:
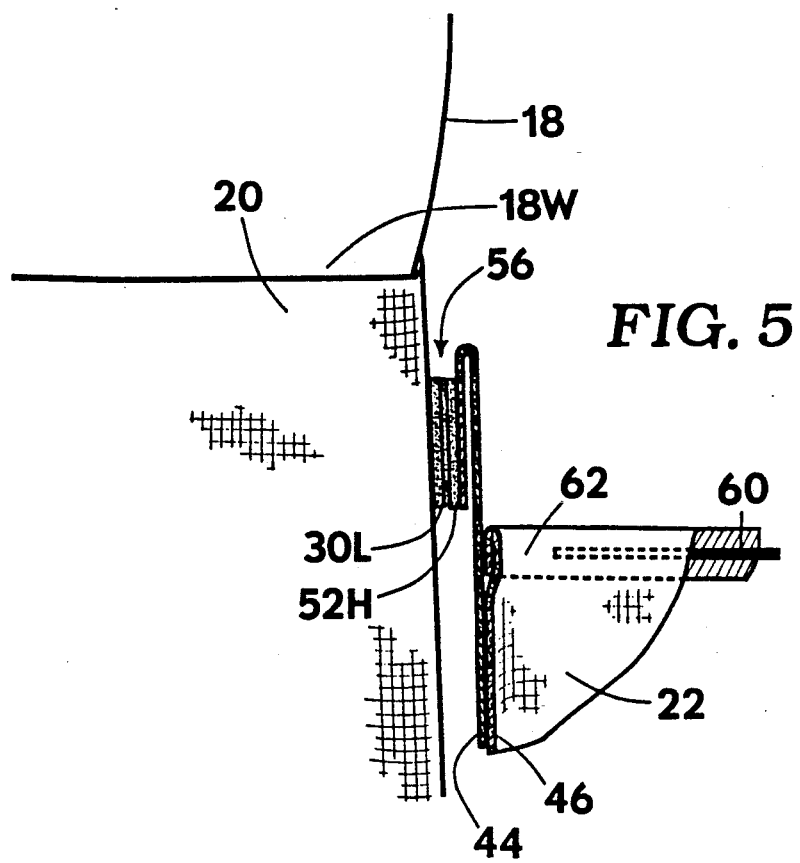
FIG. 5 is an enlarged cross sectional of the releasable attaching arrangement for attaching the convertible receptacle upon the shielding member taken along line 5—5 of FIG. 2.

Now making reference to FIG. 4, FIG. 5, and FIG. 12, convertible receptacle 22 may further have added formable semi-rigid reinforcement to a portion of the surrounding edge of opening 50. This reinforcement as shown in FIG. 5, a cross sectional view of convertible receptacle 22 along lines 5—5 of FIG. 2, is comprised of a length of ordinary solid electrical type wire 60 enclosed inside a hem 62. Wire 60 is of approximately 14 gauge size having a thin plastic insulation coating. Hem 62 is approximately 5 to 8 millimeters wide and formed along the entire top edge 46T of panel 46.

Hem 62 is accomplished easiest before panel 46 is united to panel 44. Also at this time when hem 62 is accomplished, wire 60 is inserted inside hem 62. Wire 60 is of a length approximately 10 to 15 millimeters shorter than the length of hem 62. Wire 60 is placed inside of hem 62 and centered between the ends of hem 62 leaving approximately 5 to 8 millimeters of empty hem on each end of wire 60. This re-inforcement will keep opening 50 from inadvertently collapsing while assisting in supporting a disposable waste receiver in an open and receiving manner inside convertible receptacle 22.

Figure 6:
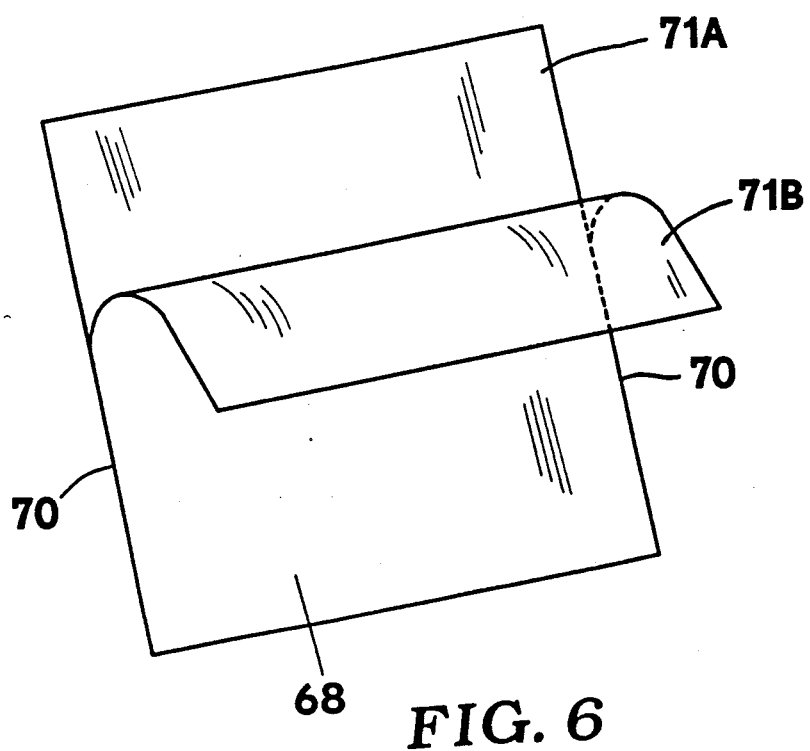
FIG. 6 is a plan view of a disposable waste receiver for placement inside convertible receptacle opening.
Figure 7:
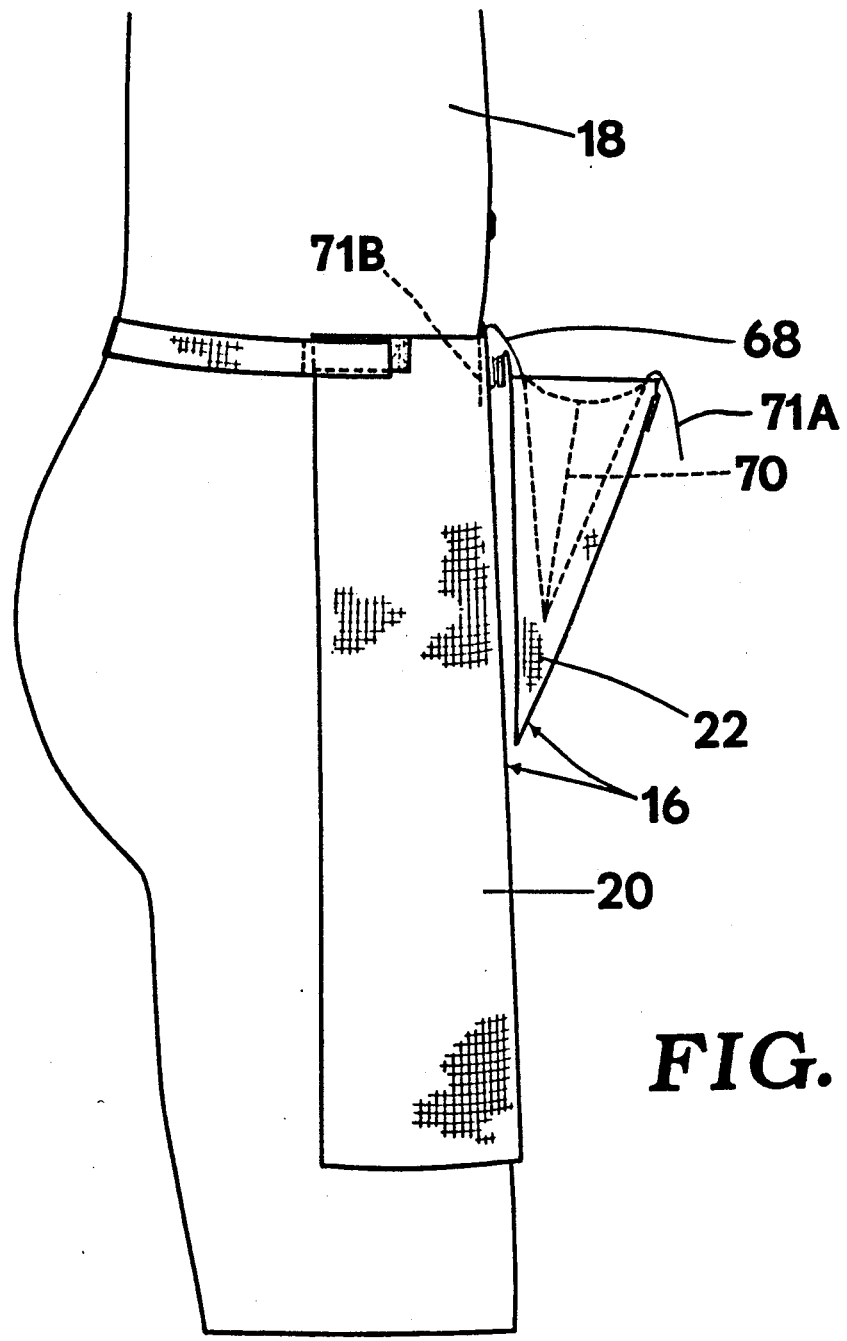
FIG. 7 is a side view of the present invention, being worn by an ostomate, further including a disposable waste receiver supported by the convertible receptacle.

Looking at FIG. 6 and FIG. 7, a disposable waste receiver 68 is shown. Disposable waste receiver 68 characterizes a small plastic ordinary kitchen type waste or storage bag. Side seams 70 are cut or separated approximately one-third of the way down, as depicted in FIG. 6, to form two identical flaps indicated at 71A and 71B. Disposable waste receiver supported 68 is to be inside convertible receptacle 22 while performing maintenance procedures, as will be explained in the operation section.

The present invention as shown in the preceding drawings and description there-of will assist the ostomate in performing a wide variety of functions pertinent to their ostomy.

OPERATION OF INVENTION

Turning now to FIG. 1, and FIG. 2, as well as FIG. 6 and FIG. 7, in use, ostomate 18 secures shielding member 20, of the present invention, around their waist 18W using releasable adjustable securing arrangement comprising of strap 32 and releasable adherence material segments 36H and 36L. Ostomate 18 holds corner 40A of shielding member 20 to their waist 18W, preferably on the right side of waist 18W, with inner surface 20A of shielding member 20 confronting waist 18W and the front lower torso area of ostomate 18. Ostomate 18 then stretches and wraps strap 32 around behind and across their lower back and waist 18W, with inner surface 42 of strap 32 confronting ostomate 18, bringing end 38A to meet with corner 40A of shielding member 20. Segments 36H and 36L are then pressed against each other adhering the two segments thereby securing shielding member 20 around waist 18W of ostomate 18. Convertible receptacle 22, of the present invention, is then attached to shielding member 20 as shown in FIG. 1, FIG. 2 and FIG. 5, the latter showing a cross sectional view of releasable attaching arrangement 56 for attaching convertible receptacle 22 to shielding member 20. Ostomate 18 folds upper edge 44T, of back panel 44, along with segment 52H backwards and away from opening 50 and then by pressing segment 52H to segment 30L the ostomate attaches convertible receptacle 22 upon shielding member 20 thereby using the releasable attaching arrangement 56 as shown in FIG. 5.

Shielding member 20 with convertible receptacle 22 attached may now be positioned around waist 18W of ostomate 18, by simply sliding shielding member 20 around waist 18W, so that convertible receptacle 22 is centered slightly below ostomy appliance 64 as is shown in FIG. 1 with a portion of the pouch of ostomy appliance 64 inside opening 50 of convertible receptacle 22.

The present invention can be used by any type of ostomate. The location of an ostomates stoma and ostomy appliance, whether on the left or right side of their abdomen is of no consequences to the ostomate utilizing the beneficial objectives of the present invention. The present invention is designed to work so that shielding member 20 with convertible receptacle 22 attached may be positioned anywhere around waist 18W of ostomate 18 by sliding shielding member 20 around to the desired location on waist 18W.

Referring to FIG. 6 and FIG. 7, disposable waste receiver 68 is supported inside opening 50 of convertible receptacle 22.

Disposable liner 68 is of the type characterizing an ordinary small plastic kitchen type waste or storage bag as described early in the description section. Ostomate 18 places disposable waste receiver 68 inside opening 50 of convertible receptacle 22 after convertible receptacle 22 has been attached to shielding member 20. Disposable waste receiver 68, having side seams 70 cut or separated one-third of the way down forming two flaps 71A and 71B, may be supported inside convertible receptacle 22 as the view in FIG. 7 shows with one flap, either 71A or 71B of disposable waste receiver 68, shown here 71B, tucked between waist 18W of ostomate 18 and shielding member 20 and the remaining flap 71A or 71B shown here 71A, which ever one remains draped over the outward front edge of opening 50, of convertible receptacle 22, and covering segment 54L.

The ostomate may now proceed with removing and replacing their ostomy appliance 64 or other hygiene or maintenance procedures needed. Any stomal discharge that occurs will fall harmlessly into disposable liner 68 and be collectively held there until maintenance procedures are completed and a new ostomy appliance has been installed around stoma 66. Also any refuse like wrappers, tape, used ostomy appliance, and any other by-products of this procedure is placed inside disposable liner 68.

When all finished and a new ostomy appliance has been installed, ostomate 18 removes disposable waste receiver 68 from convertible receptacle 22. Ostomate 18 then ties or closes off the opening of disposable waste receiver 68 and discards disposable waste receiver 68 in the trash. Ostomate 18 then removes convertible receptacle 22 from shielding member 20 by simply pulling it away from shielding member 20. Ostomate 18 then removes shielding member 20 from around waist 18W by releasing segment 36L from segment 36H.

When all finished and the present invention has been removed from the ostomate, the ostomate may convert convertible receptacle 22 to a storage receptacle. Referring now to FIG. 10 and FIG. 12, convertible receptacle 22 is converted by use of the closure arrangement 58 fixed upon convertible receptacle 22. FIG. 10 and FIG. 12 make reference to the closure arrangement 58. Shielding member 20 is placed inside opening 50 of convertible receptacle 22. Segment 52H, of releasable adherence material fixed upon back panel 44 of convertible receptacle 22, is folded forward and over opening 50 and adhered to segment 54L by pressing the two segments, 52H and 54L, together.

As shown in FIG. 12, after shielding member 20 is placed inside convertible receptacle 22 for storage, there is extra space 72 left inside convertible receptacle. Extra space 72 may be utilized for storage of ostomy appliance supplies. When utilizing closure arrangement 58 and converting convertible receptacle 22 into a storage receptacle, the ostomate has made the present invention now self containing and may be used as an ostomy and ostomy appliance maintenance kit.

SUMMARY, RAMIFICATIONS, AND SCOPE

Accordingly, the reader will see that the present invention provides an ostomate with a highly reliable device in which to deal with the formentioned problems and overcome a lack of provisions for them. The present invention will protectively shield the ostomate from becoming soiled during maintenance procedures to their stoma. In addition, the present invention will catch and receive any stomal discharge and any other refuse involved during ostomy appliance removal and replacement and hold for disposal upon completion of procedure. The convertible receptacle will store the shielding member of the present invention along with some ostomy supplies for future use while keeping the ostomy appliance supplies from the view of others. Furthermore, the present invention has the additional advantages of use by an ostomate in that;

it permits the ostomate to spend as much time as needed to perform maintenance procedures to their stoma and ostomy appliance while their ostomy appliance is removed;

it permits a new ostomate to psychologically adjust to their new bodily functions in a more timely manner assisting them to learn an efficient non-messy routine of ostomy maintenance;

it provides an ostomate with a compact overnight travel ostomy maintenance kit;

it provides the ostomate with a washable and reusable ostomy maintenance apparatus;

it permits the non-messy removal and replacement of ostomy appliances fitted over their stoma;

it provides non collapsible use of a disposable waste receiver whereby the opening of the disposable waste receiver will stay in an open and receivable manner until intentional sealing of the opening.

While my above description contains many specifics, the reader should not construe these as limitations on the scope of the present invention, but merely as exemplifications of a preferred embodiment thereof.

Those skilled in the art of the present invention should envision many other possible variations that are within the scope of the present invention. For example skilled artisans will be able to make variations in the releasable adherence material used in securing shielding member 20 around waist 18W of ostomate 18, attaching convertible receptacle 22 to shielding member 20, and in closure arrangement 58 in which convertible receptacle 22 is converted into a storage receptacle.

Buttons, snaps, zippers, hooks, ties and most all types of releasable fasteners may be alternatively substituted in place of the "Velcro" material in the above description of a preferred embodiment of the present invention.

Alternative materials may be used to construct shielding member 20 of the present invention although the material should be of durable quality and comfortable to wear for example knit type materials, cotton type materials, canvas type fabrics, flexible vinyl material, and any other suitable materials of this type.

Shielding member 20 may be constructed in many various sizes and shapes to accommodate a wide variety of waist sizes.

An elastic waistband may be constructed into and along upper edge 26 of shielding member 20 for added adjustability to waist sizes.

Strap 32 may be made of a greater or lesser length depending on the ostomates waist size.

Shielding member 20 may include tie straps as the adjustable releasable securing arrangement to secure shielding member 20 around waist 18W of ostomate 18.

Shielding member 20 may also be made to fully encircle waist 18 of ostomate 20, as to resemble a skirt.

Convertible receptacle 22 may be made from alternative materials, but material used should be of a durable, waterproof, and lightweight nature.

The present invention may also be made cosmetically attractive with decorations, patterned or printed material used in constructing either or both shielding member 20 and/or convertible receptacle 22.

There are alternative methods to construct convertible receptacle 22. Persons skilled in the art will be able to envision many of these, with one being of single panel construction where a single panel of material is cut to a determined shape then folded and sewn or bonded in ways to form the main body of convertible receptacle 22.

Skilled artisans will also be able to envision alternatives to the preferred embodiment of closure arrangement 58 for temporary conversion of convertible receptacle 22 to a storage receptacle and in releasable attaching arrangement 56.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense.

It should thus be evident that an apparatus constructed according to the concept of the present invention, or reasonably equivalent thereto, will accomplish the objects of the present invention and otherwise substantially improve the art of maintenance procedures used by ostomates on and involving their stoma and ostomy appliances.

Thus the scope of the invention should be determined by the appended claims and their legal equivalents, rather than by the examples given.

I claim:

1. An apparatus for an individual having a surgical stoma and an ostomy appliance fitted thereover for collection of bodily waste material, said apparatus for use in the maintenance procedures of said stoma and said ostomy appliance, said apparatus comprising:

a shielding member made of flexible material, said shielding member being of sufficient size to at least cover a front portion of the lower torso of said individual, said shielding member having an inner and an opposite outer surface, a receptacle of flexible material including an opening at an upper portion of said receptacle, said receptacle being of sufficient size for holding said disposable thin plastic waste receiver means for receiving waste material during and resulting from said maintenance procedures, said receptacle being of sufficient size to receive and store said shielding member when unsecured from the waist of said individual, a disposable thin plastic waste receiver means for receiving waste materials therein, releasable securing means for releasably securing said shielding member at a waist area of said individual slightly below a stoma region of said individual with said shielding member depending downwardly from said waist area while covering at least a front portion of the lower torso of said individual with said inner surface of said shielding member confronting said individual, combined attaching and closing means being interchangeably deployable for temporarily attaching said receptacle upon the outer surface of said shielding member and for temporarily closing said opening of said receptacle after said receptacle has received said shielding member for storage purposes, said combined attaching and closing means being used at non-coinciding intervals between attaching said receptacle to said shielding member and closing said opening of said receptacle, and reinforcing means at said opening of said receptacle for adding formable rigidity to the perimeter of said opening while supporting said disposable thin plastic waste receiver means inside said receptacle in an open, waste receiving manner, thereby discouraging said opening of said receptacle from inadvertently collapsing while said disposable thin plastic waste receiver means is supported and held inside said receptacle in an open waste-receiving manner during said maintenance procedures.

2. The apparatus of claim 1 wherein said receptacle is made of thin flexible vinyl material.

3. The apparatus of claim 1 wherein said shielding member is made of thin flexible plastic vinyl material.

4. The apparatus of claim 1 wherein said shielding member is made of terrycloth material.

5. The apparatus of claim 1 wherein said shielding member is of sufficient size to completely encircle the waist area of said individual.

6. The apparatus of claim 1 wherein said receptacle is of a sufficient size to store a quantity of ostomy supplies along with said shielding member.

7. The apparatus of claim 1 wherein said disposable thin plastic waste receiver means is of sufficient size to receive and hold for disposal a quantity of waste materials involved during and resulting from said maintenance procedures, said disposable thin plastic waste receiver means being of a style removable from the receptacle upon completion of said maintenance procedures, thereby keeping said receptacle clean while providing a sanitary and efficient disposal of said waste materials.

8. The apparatus of claim 7 wherein said shielding member is of generally rectangular shape, said releasable securing means further comprises: an adjusting means for adjustment of said securing means and shielding member to accommodate a wide range of waist sizes while enabling the positioning of the releasably secured shielding member at the waist of said individual, said releasable securing means with adjusting means further includes a length of elastic band attached at one end to an upper corner of said shielding member, a length of hook and loop fastener material affixed to said elastic band at an opposite end from said attached end, a length of hook and loop fastener material affixed to the outer surface of said shielding member at the opposite upper corner across from said upper corner of said shielding member where said elastic band is attached, said lengths of hook and loop fastener material attached upon said elastic band and said upper corner of said shielding member being adherently cooperative to one another, whereby said adjustable releasable securing means secures said shielding member while frictionally engaging the individuals waist.

9. The apparatus of claim 8 wherein said reinforcing means at said opening of said receptacle includes a length of formable wire approximately 14 gauge size, a small passage duct surrounding the opening of said receptacle for receiving said formable wire, whereby said opening can be shaped in ways to support said disposable thin plastic waste receiver means in an open waste receiving manner while eliminating collapsing of said opening during said maintenance procedures.

* * * * *